US00PP08251P

United States Patent [19]

Dehan

[11] Patent Number: Plant 8,251

[45] Date of Patent: Jun. 8, 1993

[54] IMPATIENS PLANT NAMED DANGAL

[75] Inventor: Klara Dehan, Holon, Israel

[73] Assignee: Danziger "Dan" Flower Farm, Moshay Mishmar Hashiva, Israel

[21] Appl. No.: 743,125

[22] Filed: Aug. 9, 1991

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

A new cultivar of Impatiens plant named Dangal characterized by its medium tall plant height, very large round flowers, bright red-purple flower color, small medium dark green foliage, excellent branching, and floriferous habit.

1 Drawing Sheet

The present invention relates to a new and distinctive cultivar of Impatiens plant, botanically known as Impatiens, commonly known as New Guinia impatiens, and referred to by the cultivar name Dangal. The new cultivar was developed by me through controlled breeding by crossing the cultivar identified by the breeding number 36-22 as the female parent with the cultivar identified 60-198 as the male parent. Both parents are unreleased, proprietary lines.

Asexual reproduction by cuttings taken at Mishmar Hashiva, Israel has shown that the unique features of this new impatiens are stabilized and are reproduced true to type in successive propagations. The cuttings preferably comprise tip cuttings with at least one axillary bud, which is vegetative and not a flower bud.

The following characteristics distinguish the new impatiens from both its parent varieties and other cultivated impatiens of this type known and used in the floriculture industry:

1. Medium tall plant height.
2. Very large round flowers.
3. Bright red-purple flower color.
4. Small, medium dark green foliage.
5. Very floriferous habit.
6. Excellent branching.
7. Permits relatively high production of cuttings.

The accompanying colored photographic drawings illustrate the overall appearance of this cultivar, showing the colors as true as it is reasonably possible to obtain in colored reproductions of this type. The photograph at the top of the sheet is a top perspective view of a portion of a plant of Dangal, and the bottom photo comprises an enlarged showing of the flowers.

The following is a detailed description of my new impatiens cultivar based on plants produced under commercial practice in Mishmar Hashiva, Israel.

The description was made both in the summer and the winter, with no differences being observed between the growing seasons in Israel, except the rate of growing and earliness in flowering in the summer.

Color references are made to The Royal Horticultural Society Colour Chart except where general terms of ordinary dictionary significance are used.

Dangal can be compared with the cultivar Argus. The flower color of Dangal is slightly darker, and the leaves of Dangal are both smaller and darker. Further, the growth habits of the respective cultivars are distinctly different.

Parentage:

*Male parent.*—60-198.

*Female parent.*—36-22.

Propagation:

A. *Type cutting.*—Leaves without flower buds.

B. *Time to initiate roots.*—8–10 days both at 25°–30° C. summer, and 20°–22° C. winter.

C. *Rooting habit.*—Good root initiation.

Plant description:

*Form.*—Medium tall, mounded, symmetrical.

B. *Habit of growth.*—Excellent branching and thus very floriferous; high cutting production.

C. *Foliage description.*—(1) Size: Relatively small, 6.0 cm in length and 3.0 cm in width. (2) Shape: Oval. (3) Margin: Finely serrated. (4) Color: Young foliage top side 137A; under side 146A; mature foliage top side 137B; under side 146B. (5) Venation: The main vein is yellowish on the top side, and slightly red on the underside.

Flowering description:

A. *Flowering habits.*—Time required for opening from bud to flower is about 4–5 days.

B. *Natural flowering season.*—Natural flowering in the spring and summer in moderate climates. In Israel flowering also occurs in the winter.

C. Flower buds: Typical. Spurs up to 6.0 cm long on mature buds with throat originating from major sepal; the wide part of the spur is spear shapen, 2.0 cm by 1.0 cm in dimension and close to 67D in color; the long part is approximately 4.0 cm in length, almost straight, and purple 60C-D.

D. *Flowers borne.*—Flower buds are presented at the tips of stems overlying the terminal whorls of leaves. At most stems, there are generally about 4–6 buds in different stages of maturity, and normally about 1–2 or more open blooms, as the plant reaches market stage. Total inflorescence after three months from planting is about 30–40 flowers.

E. *Quantity of flowers.*—Very floriferous. Flowering is continuous at temperatures above approximately 10° C. and with at least minimum levels of light.

F. *Petals.*—(1) Shape: There are two pairs of petals, each pair being generally heart shaped but somewhat asymetrical, and a single petal which is generally oval to round. (2) Color: Top side in spring when opening is 57A, fading to 53C; under side 53D with some fading on maturity (3) Number of petals: Five. (4) Size of flowers: Approximately 6.0 cm in diameter.

G. *Reproductive organs.*—(1) Stamens: One in number. (a) Anther color: White. (b) Pollen color: White. (2) Pistils: (a) Stigma: Cone shaped; green in color. (b) Style: Green in color. (c) Ovaries: One in number; size 1.5 mm, color green.

Disease resistance: Good to date.

Other important characteristics: The color of the branches are green infused with red.

I claim:

1. A new and distinct cultivar of Impatiens plant named Dangal, as illustrated and described.

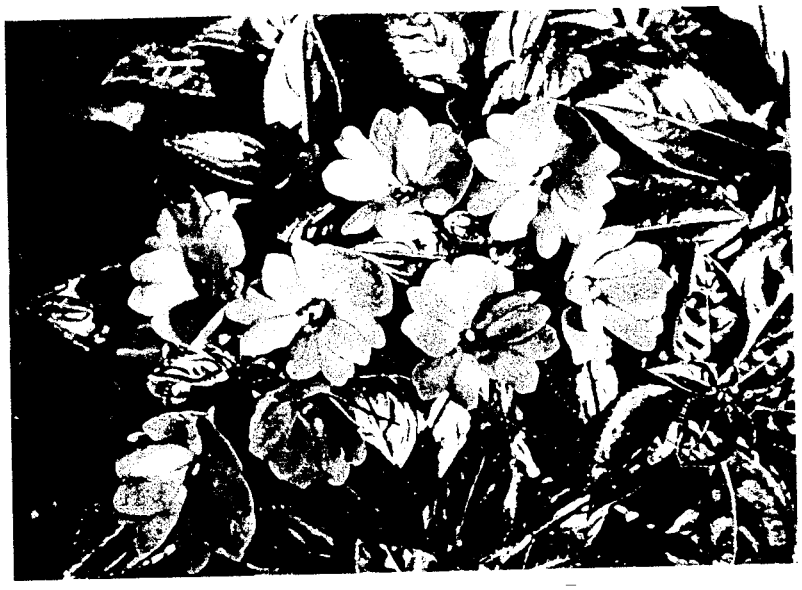
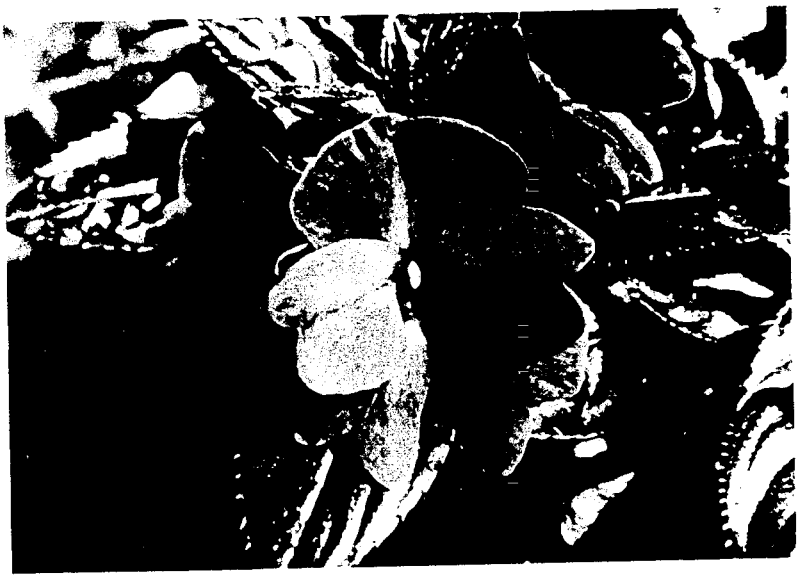

* * * * *